United States Patent
He et al.

(10) Patent No.: US 11,911,426 B2
(45) Date of Patent: Feb. 27, 2024

(54) USE OF A PLANT IN PREPARATION OF MEDICINES AND HEALTH PRODUCTS FOR PREVENTING AND TREATING OVARIAN INJURY

(71) Applicant: Ningxia Medical University, Ningxia (CN)

(72) Inventors: Rui He, Ningxia (CN); Guangyong Li, Ningxia (CN); Puguang Yu, Ningxia (CN); Yang Niu, Ningxia (CN); Huiming Ma, Ningxia (CN)

(73) Assignee: Ningxia Medical University, Yinchua (CN)

( * ) Notice: Subject to any disclaimer, the term of this patent is extended or adjusted under 35 U.S.C. 154(b) by 43 days.

(21) Appl. No.: 17/344,008

(22) Filed: Jun. 10, 2021

(65) Prior Publication Data
US 2021/0386810 A1  Dec. 16, 2021

(30) Foreign Application Priority Data

Jun. 10, 2020 (CN) .......................... 202010524177.7
Jun. 10, 2020 (CN) .......................... 202010525295.X
Jun. 10, 2020 (CN) .......................... 202010525304.5
Jun. 10, 2020 (CN) .......................... 202010525333.1

(51) Int. Cl.
| A61K 36/185 | (2006.01) |
| A61P 5/24 | (2006.01) |
| A61P 5/30 | (2006.01) |
| A61P 15/08 | (2006.01) |

(52) U.S. Cl.
CPC .............. *A61K 36/185* (2013.01); *A61P 5/24* (2018.01); *A61P 5/30* (2018.01); *A61P 15/08* (2018.01)

(58) Field of Classification Search
None
See application file for complete search history.

(56) References Cited

FOREIGN PATENT DOCUMENTS

| CN | 110025642 A | 7/2019 |
| CN | 110075139 A | 8/2019 |
| JP | 2007023012 A | 2/2007 |

OTHER PUBLICATIONS

Raskin et al. (2004) Current Pharma. Design 10, 3419-3429. (Year: 2004).*
Revilla et al. (1998) J. Agric. Food Chem. 46, 4592-4597. (Year: 1998).*
Gatlan et al. (2021) Int. J. Environ. Res. Public Health, 19, 8986. (Year: 2021).*
Wani et al. (2016) Cogent Food & Agric. 2;1, 1128519 (9 Pages) (Year: 2016).*
Xuqian Wang, Chinese Medicine Food Therapy, Beijing: China Chinese Medicine Press (Oct. 2015), English Translation provided.
Sulin Wu, Simultaneous determination of isorhamnetin, quercetin and total flavonoids in sea buckthorn pulp by reversed-phase, HPLC, National Seabuckthorn Products Testing Center—Beijing 102600, China, English Translation provided.
Elkady et al., Effects of quercetin and rosuvastatin each alone or in combination on cyclophosphamide-induced premature ovarian failure in female albino mice, Human and Experimental Toxicology (2019), XX(X):1-13.
Xu et al., Mechanism of ovarian damage caused by radiotherapy and its histological changes, Reproduction Center, Department of Obstetrics and Gynecology, Qilu Hospital, Shandong University (250012), English Translation provided.
Exploration of the protective effect and mechanism of sea buckthorn seed oil fat milk on radiotherapy and chemotherapy injury in mice, English Translation provided.
Yu Wang, Prevention of chemotherapy-induced ovarian damage in patients with gynecological malignant tumors, China Academic Journal Electronic Publishing House (2019), 631-635, English Abstract included.

* cited by examiner

*Primary Examiner* — Russell G Fiebig
(74) *Attorney, Agent, or Firm* — K&L Gates LLP

(57) ABSTRACT

The disclosure provides the use of a plant in the preparation of medicines and health products for preventing and treating ovarian injury. The application found that seabuckthorn fruit pulp and seabuckthorn seed oil have good preventive and therapeutic effects on ovarian injury. Seabuckthorn fruit pulp and seabuckthorn seed oil can prevent mouse ovarian injury and estrus cycle disorders, and can improve ovarian reserve, etc. Meanwhile, they also have good therapeutic effects on the above-mentioned injuries. This application provides a basis for the prevention and treatment of ovarian injury directly by seabuckthorn fruit pulp and seabuckthorn seed oil.

4 Claims, 6 Drawing Sheets

USE OF A PLANT IN PREPARATION OF MEDICINES AND HEALTH PRODUCTS FOR PREVENTING AND TREATING OVARIAN INJURY

This invention was made with support of the Key R&D Program of Ningxia (2020BFG02010), the National Natural Science Foundation of China (31860290, 81860268), and the Excellent Young Teachers Training Fund of Ningxia (NGY2018-74).

FIELD OF TECHNOLOGY

The present application relates to the field of the use of the medicinal and edible plant in animals and humans, in particular relates to the use of a plant in the preparation of medicines and health products for preventing and treating ovarian injury.

BACKGROUND

Ovary is the main reproductive organ of female animals (including humans) and also the most important endocrine gland. Its main function is to produce ova and secrete estrogen, progestogen, and androgen, etc. Also, the ovary is the part of the female reproductive system most sensitive to external environment changes, chemotherapy and radiation, etc., so ovarian injuries often occur. Ovarian injury not only directly affects women's reproductive function, but also have an effect on their whole-body regulation. It is a major problem that seriously endangers women's physical and mental health and fertility. In recent years, due to increased environmental pollution, dietary structure and widespread use of chemotherapy drugs, the occurrence of progressive ovarian injury has been significantly increased, leading to increased female reproductive endocrine disorders and even a decline in fertility. In particular, although the use of chemotherapy drugs can partly improve the symptoms of cancer patients and prolong their lives, while killing tumor cells, the drugs also cause great damage to normal cells of the ovary and other normal tissues of the body such as the gastrointestinal tract, for example, ovarian reproductive and endocrine dysfunction, ovarian dysfunction, and even early onset of ovarian hypofunction, which may lead to infertility. Unfortunately, there is currently no good solution for such ovarian injuries. In clinical practice, a symptomatic treatment is mainly employed, such as an exogenous hormone replacement treatment for endocrine disorders, or prevention of gastrointestinal injury caused by chemoradiotherapy by using a gastric mucosal protective agent, etc. There is still a lack of a comprehensive and effective drug that can be used in injury prevention before chemotherapy and injury repairing after chemotherapy.

Therefore, there is an urgent need to explore and discover drugs and health products for the prevention and treatment of ovarian injury.

SUMMARY

The present application discloses the use of a plant in the preparation of medicines and health products for preventing and treating ovarian injury, wherein the plant is a Sea buckthorn (*Hippophae rhamnoides Linn.*).

According to an embodiment of the present application, the use of a plant in the preparation of medicines for preventing and treating ovarian injury is provided, wherein the plant is a Sea buckthorn.

According to an embodiment of the present application, the use of a plant in the preparation of health products for preventing and treating ovarian injury is provided, wherein the plant is a Sea buckthorn.

According to an embodiment of the present application, the use of a plant in the preparation of functional foods for preventing and treating ovarian injury, wherein the plant is a Sea buckthorn.

According to an embodiment of the present application, the Sea buckthorn comprises a Sea buckthorn fruit and an extract of the Sea buckthorn fruit.

According to an embodiment of the present application, the extract of the Sea buckthorn fruit comprises a Sea buckthorn fruit pulp and a Sea buckthorn seed oil.

According to an embodiment of the present application, the dosage forms of the medicines include soft capsule, dripping pill, emulsion, tablet, lotion, liniment, ointment or suppository.

According to an embodiment of the present application, the dosage forms of the health products include soft capsule, dripping pill, emulsion, tablet, lotion, liniment, ointment or suppository.

According to an embodiment of the present application, the functional foods comprise a solid form and a liquid form.

According to embodiments of the present application, the ovarian injury includes estrous cycle disorder, excessive activation and consumption of follicles, decreased follicular reserve, follicle formation disorder, follicular maturation disorder, decreased estrogen, early withdrawal of estrogen, and decreased AMH.

According to an embodiment of the present application, the use of a plant fruit oil in the preparation of medicines for preventing and treating ovarian injury is provided, wherein the plant fruit oil is Sea buckthorn seed oil.

According to an embodiment of the present application, the use of a plant fruit oil in the preparation of health products for preventing and treating ovarian injury is provided, wherein the plant fruit oil is Sea buckthorn seed oil.

According to an embodiment of the present application, the use of a plant fruit pulp in the preparation of medicines for preventing and treating ovarian injury is provided, wherein the plant fruit pulp is a Sea buckthorn fruit pulp.

According to an embodiment of the present application, the use of a plant fruitpulp in the preparation of health products for preventing and treating ovarian injury is provided, wherein the plant fruit pulp is a Sea buckthorn fruit pulp.

This application has demonstrated for the first time that Sea buckthorn fruit pulp and Sea buckthorn seed oil have the following new functions: Sea buckthorn pulp and Sea buckthorn seed oil have good preventive and therapeutic effects on ovarian injury. Seabuckthorn fruit pulp and Sea buckthorn seed oil can prevent mouse ovarian injury and estrus cycle disorders, and improve ovarian reserve, etc., and further, they have a good therapeutic effect on the above-mentioned injuries. This application provides a basis for the prevention and treatment of ovarian injury directly by Sea buckthorn fruit pulp and Sea buckthorn seed oil. In view of the similarity of mouse ovarian injury induced by radiotherapy, chemotherapy and external environment changes, Sea buckthorn fruit pulp and Sea buckthorn seed oil would have preventive, protective and therapeutic effects on ovarian injury and ovarian dysfunction caused by various external factors.

BRIEF DESCRIPTION OF THE DRAWINGS

In order to illustrate the technical solution of the present application more clearly, the drawings needed in the embodiments will be briefly explained below. It would be obvious for those of ordinary skill in the art that other accompanying drawings may be obtained on the basis of these drawings without creative labor=.

DESCRIPTION OF THE EMBODIMENTS

Figure 1:
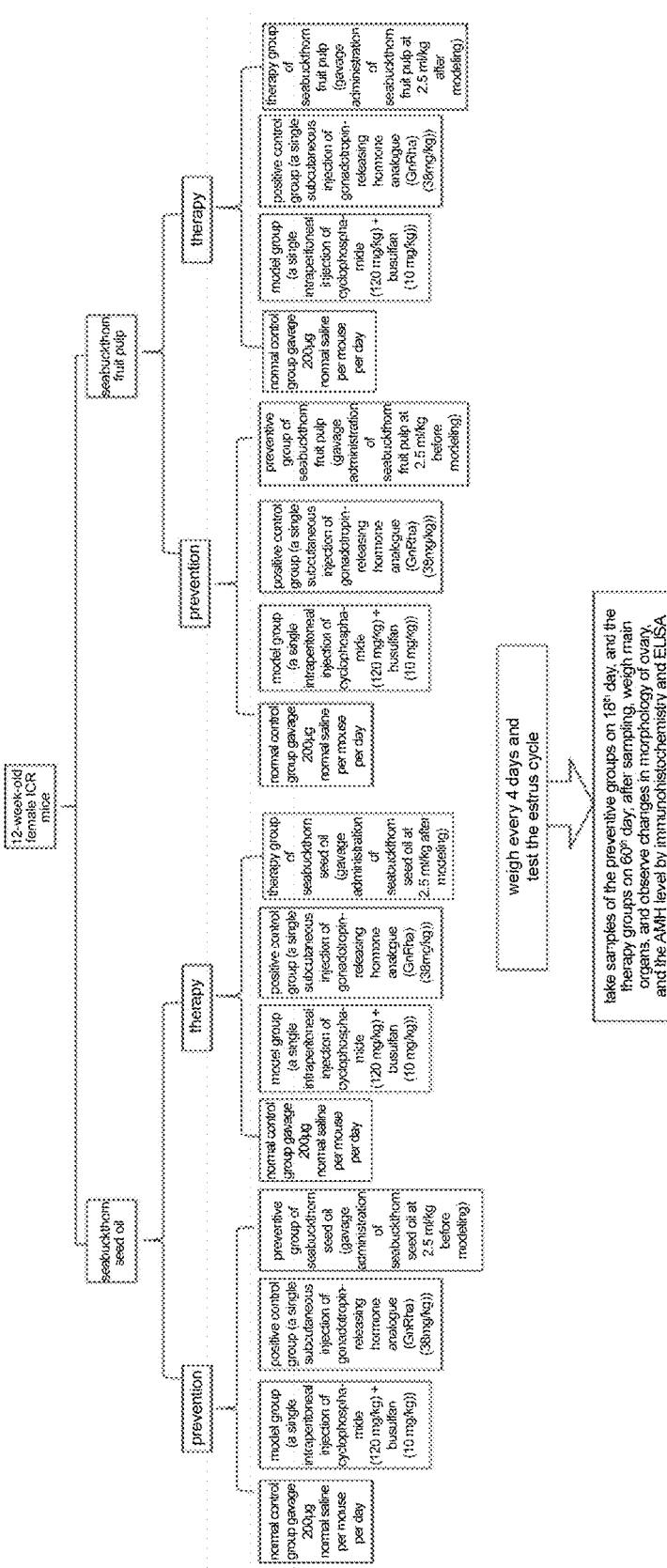
FIG. 1 is a diagram for the technical route of the application.

The embodiments of the application provide the use of a plant in the preparation of medicines for preventing ovarian injury, and the plant is a Sea buckthorn.

The embodiments of the application provide the use of a plant in the preparation of health products for treating ovarian injury, and the plant is a Sea buckthorn.

The embodiments of the application provide the use of a plant in the preparation of functional foods for preventing and treating ovarian injury, wherein the plant is a Sea buckthorn.

Preferably, the Sea buckthorn comprises a Sea buckthorn fruit and an extract of the Sea buckthorn fruit.

More preferably, the extract of the Sea buckthorn fruit comprises a Sea buckthorn fruit pulp and a Sea buckthorn seed oil.

Further, the dosage forms of the medicines include soft capsule, dripping pill, emulsion, tablet, lotion, liniment, ointment or suppository.

Further, the dosage forms of the health products include soft capsule, dripping pill, emulsion, tablet, lotion, liniment, ointment or suppository.

Further, the functional foods comprise a solid form and a liquid form.

The embodiments of the application provide the use of a plant fruit oil or a plant fruit pulp in the preparation of medicines for preventing ovarian injury, preferably the plant fruit oil is Sea buckthorn seed oil, and the plant fruit pulp is Sea buckthorn fruit pulp.

The embodiments of the application provide the use of a plant fruit oil or a plant fruit pulp in the preparation of health products for treating ovarian injury, preferably the plant fruit oil is Sea buckthorn seed oil, and the plant fruit pulp is Sea buckthorn fruit pulp.

Preferably, the ovarian injury includes estrous cycle disorder, excessive activation and consumption of follicles, decreased follicular reserve, follicle formation disorder, follicular maturation disorder, decreased estrogen, early withdrawal of estrogen, and decreased AMH.

This application has proved for the first time that Sea buckthorn fruit pulp and Sea buckthorn seed oil have the following new functions: Sea buckthorn fruit pulp and Sea buckthorn seed oil have definite preventive and therapeutic effects on ovarian injury. Seabuckthorn fruit pulp and Sea buckthorn seed oil: 1. can be used for preventive treatment when an ovary is about to be in chemoradiotherapy and other environments that may cause ovarian damage, and have a definite protective effect to the ovary; 2: can be used for therapeutic treatment after ovarian injuries due to chemoradiotherapy and other reasons, and have a definite therapeutic effect on ovarian injury. In this application, mice with ovarian damage caused by chemoradiotherapy are used as animal model, ovarian tissue morphology and detections of estrus cycle, estrogen and AMH which represents ovarian reserve function are employed as evaluation index, and Sea buckthorn fruit pulp and Sea buckthorn seed oil are verified to have definite preventive and therapeutic effects on ovarian injury. This application provides a support for the prevention and treatment against ovarian injury directly using Sea buckthorn fruit pulp and Sea buckthorn seed oil. In view of the similarity of mouse ovarian injury induced by radiotherapy, chemotherapy and external environment changes, Sea buckthorn fruit pulp and Sea buckthorn seed oil would have preventive, protective and therapeutic effects on ovarian injury and ovarian dysfunction caused by various external factors.

Specific Implementation Methods:

1. Technical Solution (1) Establishment of an Animal Model with Ovarian Injury Induced by Chemoradiotherapy Drugs:

Chemoradiotherapeutic drug is one of the most common causes of ovarian injury. Cyclophosphamide (CY) and busulfan (BUS) are commonly used as anticancer drugs in clinic and are also representative ovarian toxic drugs. This application established a mouse model of ovarian injury with adult female mice by single intraperitoneal injection of cyclophosphamide (120 mg/kg) and busulfan (10 mg/kg).

(2) Interventions to Animal Models of Ovarian Injury Induced by Chemoradiotherapy Drugs:

This experiment verified the preventive and therapeutic effects of Sea buckthorn fruit pulp and Sea buckthorn seed oil on ovarian injury, respectively.

Preventive experiment of Sea buckthorn fruit pulp/Sea buckthorn seed oil: in this experiment, 12-week-old female ICR mice were used, and divided into normal control group, model group, preventive groups of Sea buckthorn fruit pulp/Sea buckthorn seed oil (protective groups of Sea buckthorn pulp/Sea buckthorn seed oil) and positive control group (GnRha group), 8 in each group. The mice received gavage treatment every day for 7 days before modeling, wherein the normal group, model group and positive control group were given normal saline, and the preventive group of Sea buckthorn fruit pulp and preventive group of Sea buckthorn seed oil were respectively given Sea buckthorn fruit pulp and Sea buckthorn seed oil at a dose of 2.5 ml/kg. Except the normal group, mice in the model group and preventive groups of Sea buckthorn fruit pulp and Sea buckthorn seed oil were given single intraperitoneal injection of cyclophosphamide (120 mg/kg) and busulfan (10 mg/kg) on the 8th day to establish the mouse model of ovarian injury. The model group and the normal control group were given normal saline gavage in the early stage to ensure in consistent with the preventive groups of Sea buckthorn fruit pulp and Sea buckthorn seed oil, thereby avoiding the difference caused by the gavage operation. After the model was successfully established in the preventive groups of Sea buckthorn fruit pulp and Sea buckthorn seed oil, the mice respectively received gavage administration of Sea buckthorn seed oil or Sea buckthorn fruit pulp at 2.5 ml/kg every day until the 18th day. The positive control group (GnRha group) was given a single subcutaneous injection of gonadotropin-releasing hormone analogue (GnRha) (38 mg/kg) one day before modeling, and on the second day, was given a single intraperitoneal injection of cyclophosphamide (120 mg/kg) and busulfan (10 mg/kg) to establish the mouse model of ovarian injury.

Therapeutic experiment of Sea buckthorn fruit pulp/Sea buckthorn seed oil: in this experiment, 12-week-old female ICR mice were used, and divided into normal control group, model group, therapy group of Sea buckthorn fruit pulp, therapy group of Sea buckthorn seed oil, and positive control group (GnRha group), 8 per group. The normal control group was given normal saline; the model group, therapy group of Sea buckthorn fruit pulp, therapy group of Sea buckthorn seed oil, and positive control group (GnRha group) were given a single intraperitoneal injection of cyclophosphamide (120 mg/kg) and busulfan (10 mg/kg) to establish the mouse model of ovarian injury. The therapy groups of Sea buckthorn fruit pulp and Sea buckthorn seed oil respectively received gavage administration of Sea buckthorn fruit pulp or Sea buckthorn seed oil at 2.5 ml/kg every day from the first day of modeling, and sampling was conducted on the 60th day. The positive control group (GnRha group) was given a single subcutaneous injection of gonadotropin-releasing hormone analogue (GnRha) (38 mg/kg) on the first day of modeling, and then received daily gavage administration of normal saline (0.2 ml) until samples were taken on the 60th day (The purpose of the daily gavage was to ensure the consistency with the model group and the therapy group of Sea buckthorn fruit pulp so as to avoid the difference caused by the gavage operation).

The mice in the preventive groups were sampled on the 18th day, and the mice in the therapy groups were treated by gavage administration of Sea buckthorn fruit pulp and Sea buckthorn seed oil continuously and sampled on the 60th day. Mice were weighed every 4 days and their estrus cycles were surveyed during the modeling period. After sampling, histomorphological changes in the mouse ovaries of each group were examined, the number of follicles at all levels in the ovarian tissue were counted, the levels of serum estrogen (E2), follicle stimulating hormone (FSH), and anti-Müllerian hormone (AMH) were detected, and the expression level of AMH protein was detected by immunohistochemistry.

(3) Experimental Results Monitoring and Data Collection

Mice in all the groups were examined and recorded on body weight, food intake and estrous cycle changes every 4 days from 12 weeks of age until the samples were taken. The morphological changes in ovary were observed by paraffin embedding and section staining of ovarian tissue. Estrogen level in plasma was detected by ELISA, and immunohistochemistry was used to detect the AMH changes.

2. Technical Route Diagram

The technical route diagram is shown in FIG. 1.

3. Main Technique

1) Establishment of an Animal Model with Ovarian Injury Induced by Chemoradiotherapy Drugs Cyclophosphamide (CY) and busulfan (BUS) are commonly used as anticancer drugs in clinic and are also representative ovarian toxic drugs. This application established a mouse model of ovarian injury by single intraperitoneal injection of cyclophosphamide (120 mg/kg) and busulfan (10 mg/kg) into adult female mice.

2) Determination of the Estrus Cycle by Smear Method with Rinse Solution of Vaginal Exfoliated Cell A dropper was used to suck appropriate amount of normal saline, which was used for rinsing and suction of the vaginal secretions onto a glass slide at the same time points every day, and the cell morphology was observed under a microscope immediately to determine the estrus cycle.

4. Experimental Results 4.1 Seabuckthorn Fruit Pulp and Sea Buckthorn Seed Oil can Prevent and Treat Mouse Ovarian Tissue Lesions Caused by Ovarian Injury.

Follicle is the main functional unit of ovary and its periodical growth and mature require the normal functioning of pituitary gonadotropin and sex hormones. Generally, it can be divided into primordial follicle, primary follicle, secondary follicle and mature follicle according to the process of its growth and mature. Chemoradiotherapy will directly cause damage to ovarian tissue, destroy the structure of the mouse ovary, and significantly reduce the numbers of primordial follicles, growing follicles and mature follicles in the ovarian. In mice of the model group, ovarian atrophy was visible to naked eyes. The optical microscope showed ovarian structure disorders, thickened cortex, decrease of growing follicles at each stage, degenerative changes such as degeneration, pyknosis or disappearance of oocyte and its vacuole-like changes, abnormal morphology of zona pellucida, etc.; the granular cells around oocyte appeared reduced cellular layers, disordered arrangement, increased intercellular space, intracellular and intercellular edema; increase and fibrosis of corpus *luteum*; decrease of blood vessels, and fibrosis and necrosis of the mesenchyme. This application found that administration of Sea buckthorn fruit pulp and Sea buckthorn fruit oil before chemoradiotherapy has a significant preventive effect on mouse ovarian tissue lesions induced by chemoradiotherapy; for mice with ovarian injury caused by chemoradiotherapy, the pathological changes in the ovarian tissue can be significantly reversed after the treatment of Sea buckthorn fruit pulp and Sea buckthorn fruit oil.

Figure 2:
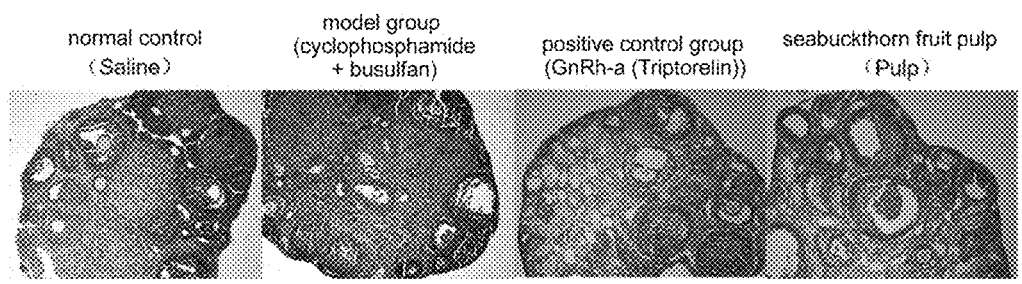
FIG. 2 shows the H&E staining results of paraffin sections of mouse ovarian tissue in the preventive experiment group of Sea buckthorn fruit pulp.
Figure 3:
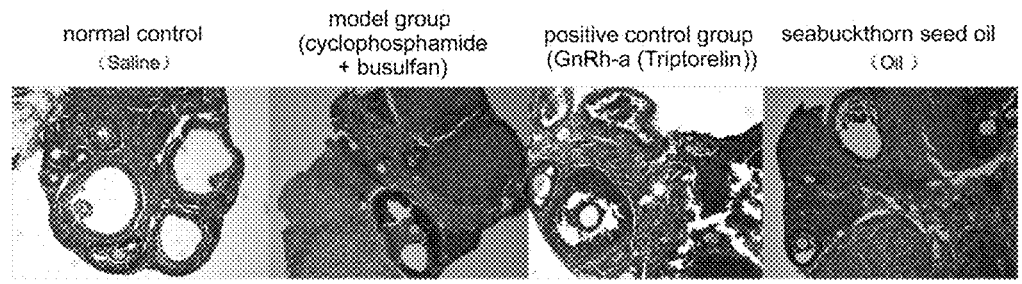
FIG. 3 shows the H&E staining results of paraffin sections of mouse ovarian tissue in the preventive experiment group of Sea buckthorn seed oil.

Preventive Experiment Results of Sea Buckthorn Fruit Pulp/Fruit Oil:

(1) Normal control group: general observation showed that the ovaries of the mice were normal in morphology and ruddy in color; as shown in FIG. 2 or FIG. 3, after HE staining, multiple follicles of different growth stages can be seen, and the granular cells has intact morphology and are regularly arranged, most of them containing 8-9 layers;

(2) Model group: General observation showed that the ovaries of the mice were atrophied and the surface was pale. As shown in FIG. 2 or FIG. 3, HE staining shows ovarian structure disorder, thickened cortex, decrease of growing follicles at each stage, degenerative changes such as degeneration, pyknosis or disappearance of oocyte and its vacuole-like changes, abnormal morphology of zona pellucida, etc.; the granular cells around oocyte appear reduced cellular layers, disordered arrangement, partial exfoliation, no corona radiate, increased intercellular space, intracellular and intercellular edema; increase and fibrosis of corpus *luteum*; decrease of blood vessels, and fibrosis and necrosis of the mesenchyme;

(3) Positive control group (GnRha group): general observation showed that the ovarian tissues had morphologically intact follicles, and were similar to the normal group and normal in morphology; as shown in FIG. 2 or FIG. 3, HE staining shows that follicles and corpus *luteum* at various developmental stages are visible, and granular cells are morphologically intact and regularly arranged;

(4) Results of the preventive group of Sea buckthorn fruit pulp: General observation showed that the ovaries had smooth and ruddy surfaces and were close to normal tissues. As shown in FIG. 2, HE staining shows that primordial follicles and multiple follicles at different development stages are visible in the ovary; ootid and corona *radiata* can be seen in the follicles near mature stage; the granular cells are arranged tightly and comprise increased cell layers; and the morphology is close to the normal control group and positive control group.

(5) Results of the preventive group of Sea buckthorn seed oil: As shown in FIG. 3, multiple follicles at different development stages can be seen in the ovary; corpus *luteum* has normal structure; ootid and corona *radiata* can be seen in the follicles near mature stage; the granular cells are arranged tightly and comprise increased cell layers; the theca cell layer of follicles is relatively thinner; and the morphology is close to the normal control group and the positive control group.

Figure 4:
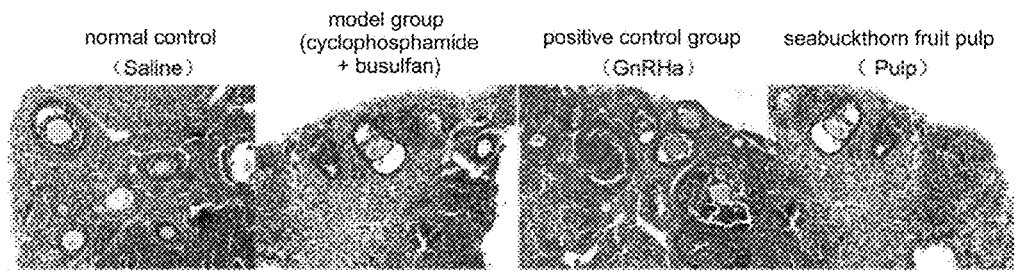
FIG. 4 shows the H&E staining results of paraffin sections of mouse ovarian tissue in the therapeutic experiment group of Sea buckthorn fruit pulp.
Figure 5:
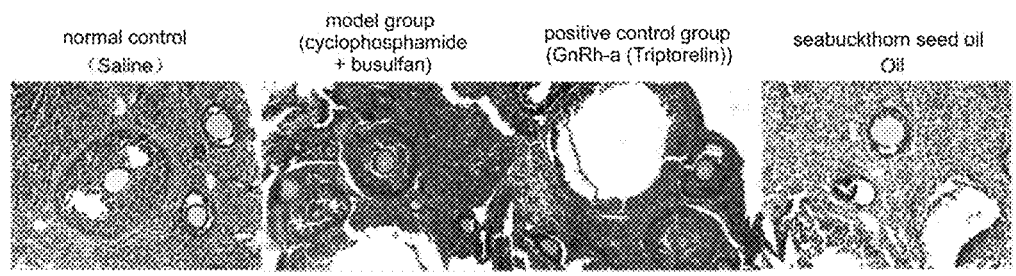
FIG. 5 shows the H&E staining results of paraffin sections of mouse ovarian tissue in the therapeutic experiment group of Sea buckthorn seed oil.

Therapeutic Experiment Results of Sea Buckthorn Fruit Pulp/Fruit Oil:

(1) Normal control group: General observation showed that the surface of the ovary was smooth and ruddy. As shown in FIG. 4 or FIG. 5, HE staining shows that follicles and corpus *luteum* at different developmental stages are visible, and granular cells are morphologically intact and regularly arranged;

(2) Model group: Visual observation showed that the ovaries reduced in size, and their surface were rough and irregular. As shown in FIG. 4 or FIG. 5, HE staining shows that under the microscope, fibrosis and hyalinization of ovarian mesenchyme are visible; most of the primordial follicles in the cortex disappear; follicles of various developmental stages are missing; a large number of normal cortical cells are lost; and the granular cells are exfoliated, and comprise decreased cell layers.

(3) Positive control group (GnRha group): general observation showed that the ovarian tissues had partial recovered follicle morphology, and were similar to the normal group; as shown in FIG. 4 or FIG. 5, HE staining shows that the follicles at various developmental stages reappear; and normal corpus *luteum* appears; the granular cells in the follicles are morphologically intact and regularly arranged;

(4) Results of the therapy group of Sea buckthorn fruit pulp: As shown in FIG. 4, in the mouse ovaries of the Sea buckthorn fruit pulp group, multiple follicles of different developmental stages are visible; there are primordial follicles in the ovarian cortex; ootid and corona *radiata* can be seen in the follicles near mature stage; the granular cells are arranged tightly and comprise increased cell layers; and the morphology is obviously restored compared with the model group, and close to the normal control group and the positive control group.

(5) Results of the therapy group of Sea buckthorn seed oil: The mouse ovarian tissues of the group were fine in histomorphology. As shown in FIG. 5, the numbers of primordial follicles, primary follicles and mature follicles and the total number of follicles in the cortex area were significantly increased; there is a significant improvement compared with the model group, and the morphology is close to the normal control group.

It can be seen from the above experimental results that both Sea buckthorn fruit pulp and Sea buckthorn seed oil can prevent and treat ovarian tissue lesions in mice caused by chemoradiotherapy.

4.2 Seabuckthorn Fruit Pulp and Sea Buckthorn Seed Oil can Prevent and Treat Mouse Estrous Cycle Disorders Caused by Ovarian Injury.

Estrus cycle refers to the time interval between the previous estrus and the next estrus of female mammal, or the time interval between the previous ovulation and the next ovulation. Usually, it is divided into proestrus (prophase of estrus), estrus, metestrus (anaphase of estrus) and diestrus (interphase) according to the physiological changes of the animal reproductive system. Regular estrus cycles are the signal for the sexual maturity of a mammal, and mean that the ovary begins to function. Disorders and even no more existence of the estrus cycle and the occurrence of continuous diestrus are the direct representation of ovarian injury. This application found that administration of Sea buckthorn fruit pulp and Sea buckthorn fruit oil before chemoradiotherapy has a significant preventive effect on ovary injury (which results in estrous cycle disorders) induced by chemoradiotherapy; for mice with ovarian injury caused by chemoradiotherapy, the estrus cycle can be significantly restored after the treatment of Sea buckthorn fruit pulp and Sea buckthorn fruit oil.

Figure 6:
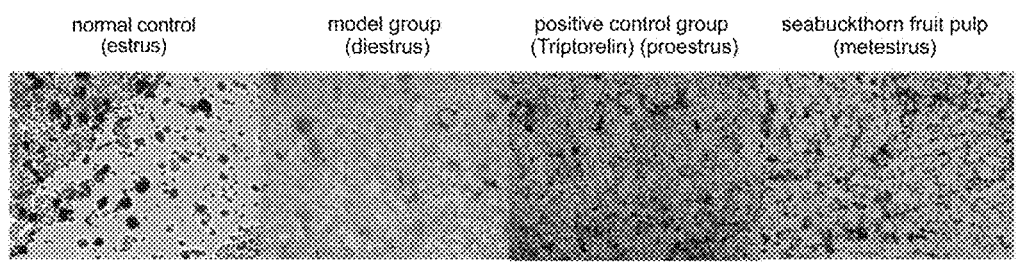
FIG. 6 shows the observation results of mouse vaginal secretions in the preventive experiment group of Sea buckthorn fruit pulp.
Figure 7:
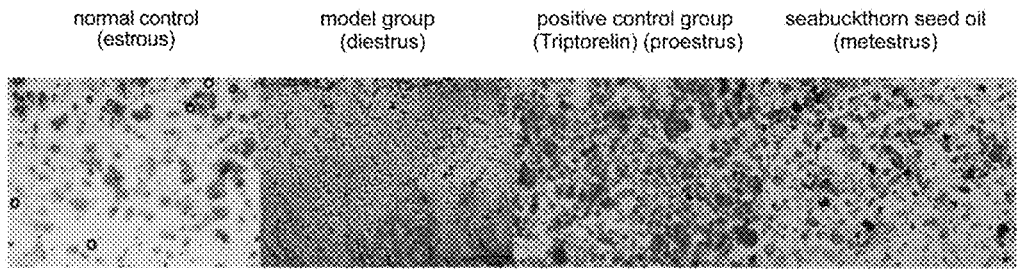
FIG. 7 shows the observation results of mouse vaginal secretions in the preventive experiment group of Sea buckthorn seed oil.

Preventive Experiment Results of Sea Buckthorn Fruit Pulp/Fruit Oil:

(1) Normal control group: There was an obvious normal estrus cycle of 4 to 5 days and the distribution of each phase was relatively equilibrium. As shown in FIG. 6 or FIG. 7, at estrus (normal control group), there are a large number of squamous epithelial cells, which are large and irregular in shape and have no nuclei, and the white blood cells disappear.

(2) Model group: Disorders and prolongation of estrus cycle occurred from 3-4 days after the administration, and continuous diestrus on the 7th day. As shown in FIG. 6 or FIG. 7, there are a large number of white blood cells and a very small amount of spindle-shaped epithelial cells, suggesting no ovulation.

(3) Positive control group (GnRha group): As shown in FIG. 6 or FIG. 7, at proestrus (positive control group), spindle-shaped epithelial cells can be seen in clusters or alone, with fewer white blood cells.

(4) Results of the preventive group of Sea buckthorn fruit pulp: the regularity of animal's estrus cycle could be protected by giving Sea buckthorn fruit pulp in advance, and there were no obvious estrus cycle disorders. As shown in FIG. 6, it is at metestrus, there are various cell types, such as white blood cells, epithelial cells whithout nuclei and spindle-shaped epithelial cells;

(5) Results of the preventive group of Sea buckthorn seed oil: the regularity of animal's estrus cycle could be protected by giving Sea buckthorn seed oil in advance, and there were no obvious estrus cycle disorders. As shown in FIG. 7, it is at metestrus, there are various cell types, such as white blood cells, epithelial cells whithout nuclei and spindle-shaped epithelial cells.

Figure 8:
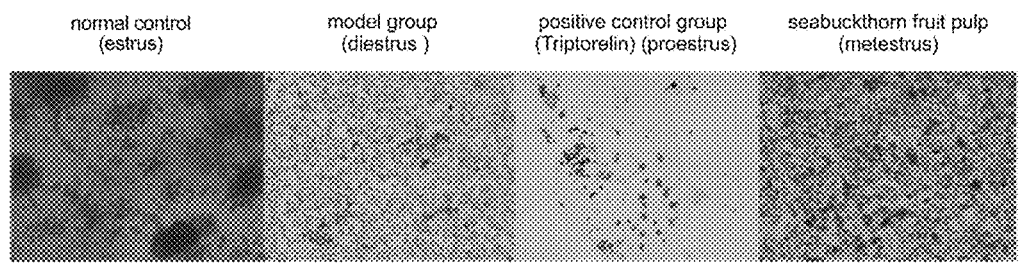
FIG. 8 shows the observation results of mouse vaginal secretions in the therapeutic experiment group of Sea buckthorn fruit pulp.
Figure 9:
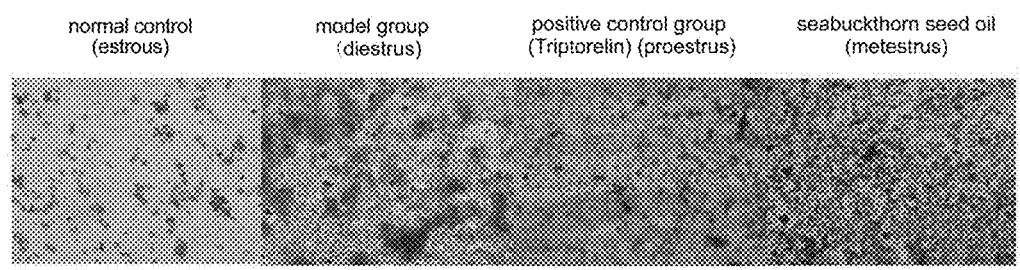
FIG. 9 shows the observation results of mouse vaginal secretions in the therapeutic experiment group of Sea buckthorn seed oil.

Therapeutic Experiment Results of Sea Buckthorn Fruit Pulp/Fruit Oil:

(1) Normal control group: The estrus cycle was regular and the distribution of each phase was relatively equilibrium. As shown in FIG. 8 or FIG. 9, at estrus (normal control group), it can be seen that squamous epithelial cells are large and irregular in shape and have no nuclei, and the white blood cells disappear.

(2) Model group: After the administration, the estrus cycle was disordered and prolonged over time, and continuous diestrus appeared on the 7th day. As shown in FIG. 8 or FIG. 9, there are a large number of white blood cells and a very small amount of spindle-shaped epithelial cells, suggesting no ovulation.

(3) Positive control group (GnRha group): As shown in FIG. 8 or FIG. 9, at proestrus (positive control group), spindle-shaped epithelial cells can be seen in clusters or alone, with fewer white blood cells. Compared with the model group, the estrus cycle has restored to a certain degree. Except for leukocytes, other cells begin to appear from 4 days after the administration, and the estrus cycle is gradually restored.

(4) Results of the therapy group of Sea buckthorn fruit pulp: The mice in the Sea buckthorn fruit pulp group that had an initial state of continuous diestrus, gradually showed cyclic changes consisting of proestrus, estrus and metestrus, and the cyclic changes became more and more regular as the treatment. As shown in FIG. 8, at metestrus (Sea buckthorn fruit pulp group), there are various cell types, such as white blood cells, epithelial cells without nuclei and spindle-shaped epithelial cells;

(5) Results of the therapy group of Sea buckthorn seed oil: After the administration of the chemoradiotherapy drugs, the mice showed estrous cycle disorders and continued diestrus. However, as the treatment of Sea buckthorn seed oil, the mice gradually recovered to have a regular estrus cycle; as shown in FIG. 9, at metestrus (therapy group of Sea buckthorn seed oil), there are various cell types, such as white blood cells, epithelial cells without nuclei and spindle-shaped epithelial cells;

From the above experimental results, it can be seen that Sea buckthorn fruit pulp and Sea buckthorn seed oil have good preventive protection and therapeutic effects on estrous cycle disorders in mice caused by ovarian injury.

4.3 Seabuckthorn Fruit Pulp and Sea Buckthorn Seed Oil can Prevent and Treat Mouse Hypoestrogenism Caused by Ovarian Injury.

Ovarian damage can cause hypoestrogenism in mice, and hypoestrogenism will further prompt ovarian failure.

This application found that administration of Sea buckthorn fruit pulp and Sea buckthorn fruit oil before ovarian injury caused by chemoradiotherapy has a significant preventive effect on hypoestrogenism induced by chemoradiotherapy; for mice that already have ovarian injury caused by chemoradiotherapy, the secretion of estrogen can be significantly restored after the treatment of Sea buckthorn fruit pulp and Sea buckthorn fruit oil.

Figure 10:
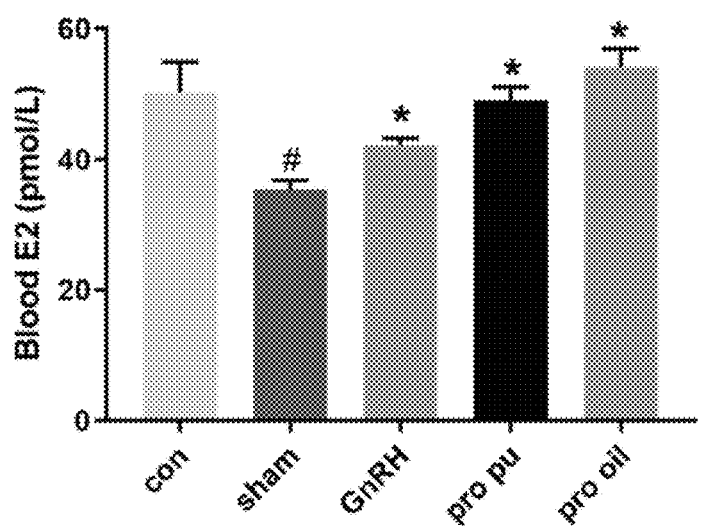
FIG. 10 shows the changes in estrogen E2 level of mice in the respective preventive experiment groups of Sea buckthorn fruit pulp and Sea buckthorn seed oil.

Preventive Experiment Results of Sea Buckthorn Fruit Pulp/Fruit Oil:

As shown in FIG. 10, the levels of estrogen E2 in mouse plasma of each group were detected. After the administration of the chemoradiotherapy drugs, the estrogen E2 level of the model group (sham group) was significantly reduced (#$p<0.05$) compared with the normal control group (con group), confirming the existence of ovarian damage. The positive control (GnRH) group partly protected the secretion of estrogen E2. However, in the two preventive groups (pro pu group and pro oil group) that were given Sea buckthorn fruit pulp and Sea buckthorn fruit oil in advance, the value of estrogen E2 was significantly higher than that of the model group, and even more approaching to the normal control group than the positive control group, and showed little influence by the chemoradiotherapy drugs (*$p<0.05$).

This has further proved that Sea buckthorn fruit pulp and Sea buckthorn seed oil and GnRHa for the positive control group all have a protective effect on estrogen secretion, and can significantly prevent ovarian injury induced by chemoradiotherapy and other factors with definite effectiveness.

Figure 11:
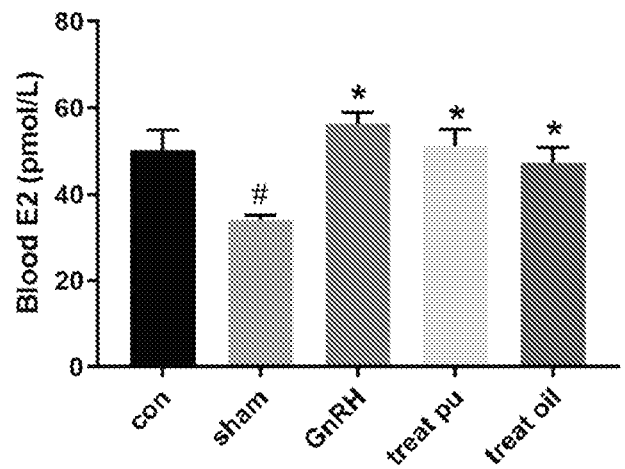
FIG. 11 shows the changes in estrogen E2 level of mice in the respective therapeutic experiment groups of Sea buckthorn fruit pulp and Sea buckthorn seed oil.

Therapeutic Experiment Results of Sea Buckthorn Fruit Pulp/Fruit Oil:

As shown in FIG. 11, after the administration of the chemoradiotherapy drugs, the level of estrogen E2 in the model group (sham group) was significantly reduced (#$p<0.05$) compared with the normal control group (con group), suggesting ovarian injury. After the treatment of Sea buckthorn fruit pulp (treat pu) and Sea buckthorn seed oil (treat oil), the value of estrogen E2 increased significantly, suggesting the recovery of the ovarian injury. The restored value of estrogen E2 was close to the positive control group (GnRH) group.

This has further proved that Sea buckthorn fruit pulp and Sea buckthorn fruit oil and GnRHa for the positive control group all have therapeutic effects on the decreased secretion of estrogen caused by ovarian injury, with definite effectiveness.

4.4 Seabuckthorn Fruit Pulp and Sea Buckthorn Seed Oil can Prevent and Treat the Decline of Ovarian Reserve in Mice Caused by Chemoradiotherapy.

Anti-Müllerian hormone (AMH) is an important indicator of ovarian reserve. Plasma AMH test can be used to quickly and reliably evaluate ovarian reserve function. We detect plasma AMH levels by ELISA method, and staining of AMH on ovarian tissue sections was performed by immunohistochemistry method.

Figure 12:
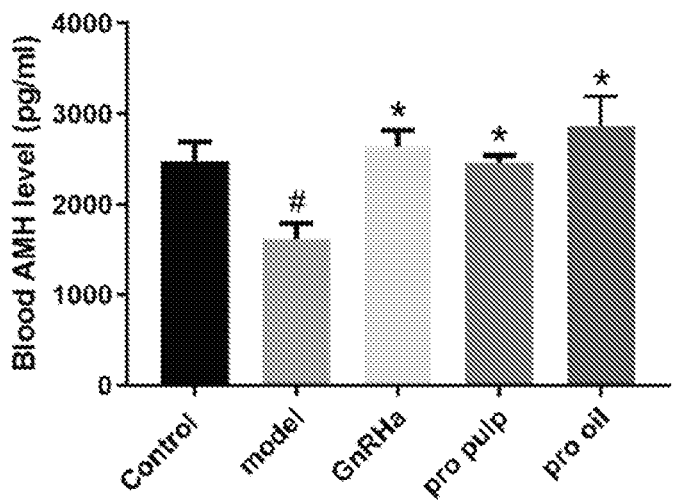
FIG. 12 shows the changes in serum AMH level of mice in each group.

Preventive Experiment Results of Sea Buckthorn Fruit Pulp/Fruit Oil:

As shown in FIG. 12, the levels of AMH in mouse plasma of each group were detected. After the administration of the chemoradiotherapy drugs, the AMH level of the model group (model group) was significantly lowered compared with that of the normal control group (Control group) (#p<0.05), which confirmed decline of the ovaries reserve function and existence of ovarian damage. The AMH secretion of the positive control (GnRHa) group was similar to that of the normal group. In the two preventive groups (pro pulp group, pro oil group) that were given Sea buckthorn fruit pulp and Sea buckthorn fruit oil in advance, the value of AMH significantly increased compared with that of the model group, and was close to the normal control group, and showed almost no influence by the chemoradiotherapy drugs (*p<0.05).

Figure 13:
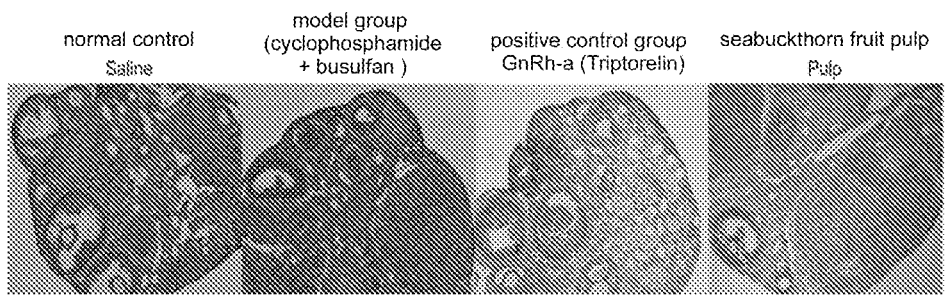
FIG. 13 shows the immunohistochemical results of AMH expression in mouse ovarian tissue in the preventive experiment group of Sea buckthorn fruit pulp.
Figure 14:
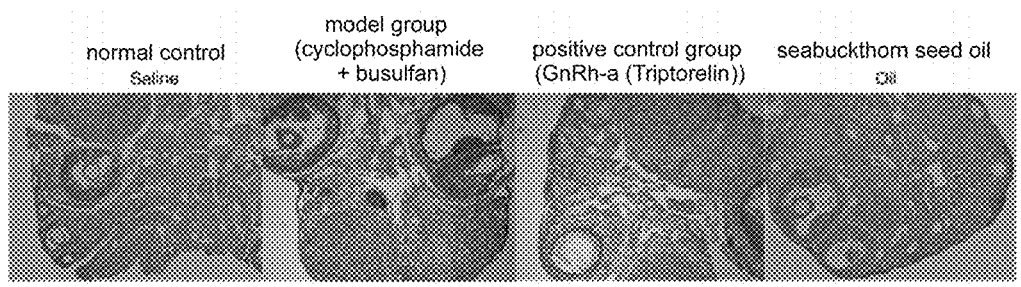
FIG. 14 shows the immunohistochemical results of AMH expression in mouse ovarian tissue in the preventive experiment group of Sea buckthorn seed oil.

The results of the immunohistochemical staining for AMH was consistent with the plasma detection by Elisa. As shown in FIGS. 13 and 14, there are uniform yellow staining among the ovarian granule cells of the mice in normal group, which proves that AMH was expressed in these parts; the mouse ovaries of the model group show not only structural changes, but also significant reduction of the yellow staining among the granule cells; the positive control group, the preventive group of Sea buckthorn seed oil, and the preventive group of Sea buckthorn fruit pulp appear uniform and high-intensity yellow staining areas among the ovarian granular cells, which show that the Sea buckthorn seeds oil and Sea buckthorn fruit pulp would have ovary-protecting effects similar to the positive control (gonadotropin-releasing hormone receptor agonist), and can significantly protect and enhance the reserve function of the damaged ovaries.

This has further proved that Sea buckthorn fruit pulp and Sea buckthorn fruit oil and GnRHa for the positive control group all have a protective effect on AMH secretion. They have significant protection effects on ovarian damage caused by factors such as chemoradiotherapy, and can protect ovarian reserve function with definite effectiveness.

Figure 15:
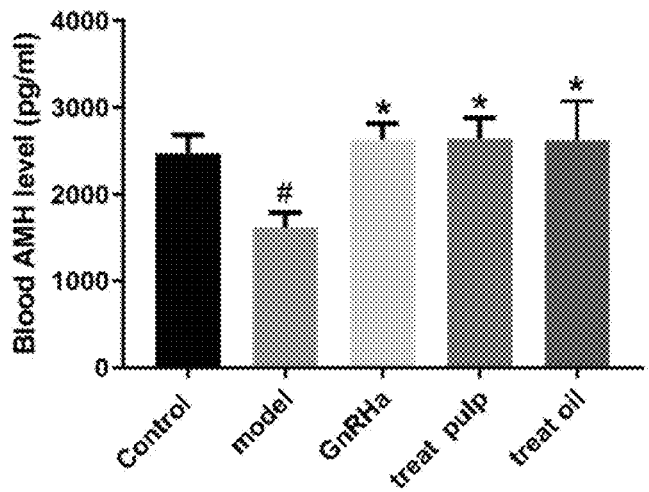
FIG. 15 shows the changes in serum AMH level of mice in each group.

Therapeutic Experiment Results of Seabuckthorn Fruit Pulp/Fruit Oil:

As shown in FIG. 15, after the administration of the chemoradiotherapy drugs, the AMH levels of the model group (model group) were significantly reduced (#p<0.05) compared with the normal control group (Control group), suggesting ovarian damage and decreased ovarian reserve. After treatment with Sea buckthorn fruit pulp (treat pulp) and Sea buckthorn seed oil (treat oil), the AMH level increased significantly, suggesting the recovery of the ovarian damage. The recovery of AMH level was similar to that of the positive control group (GnRHa).

Figure 16:
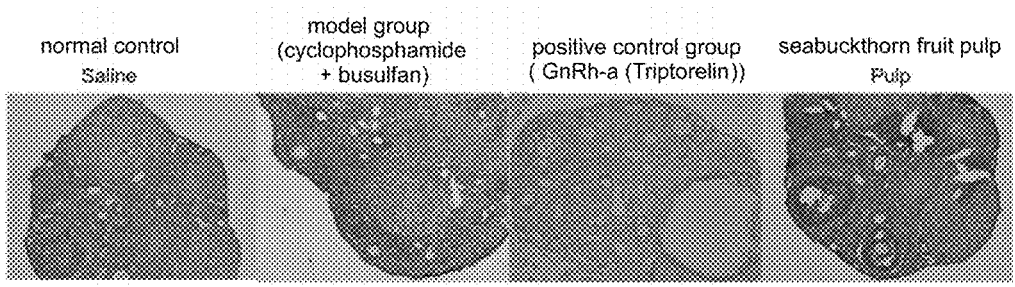
FIG. 16 shows the immunohistochemical results of AMH expression in mouse ovarian tissue in the therapeutic experiment group of Sea buckthorn fruit pulp.
Figure 17:
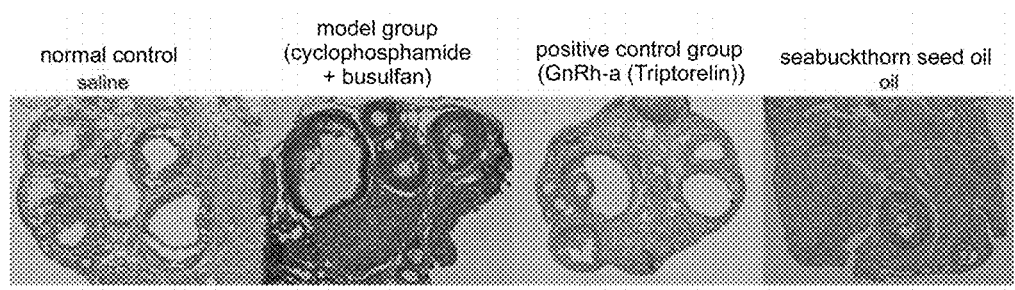
FIG. 17 shows the immunohistochemical results of AMH expression in mouse ovarian tissue in the therapeutic experiment group of Sea buckthorn seed oil.

The immunohistochemical staining for AMH was consistent with the results of the plasma detection by Elisa. As shown in FIG. 16 and FIG. 17, the expression of AMH in the model group was significantly reduced, but after the treatment with Sea buckthorn fruit pulp and Sea buckthorn fruit oil, the AMH expression level was significantly restored. The results were similar to those of the positive control (GnRHa) group.

This has further proved that Sea buckthorn fruit pulp and Sea buckthorn fruit oil and GnRHa for the positive control group all have therapeutic effects on the decrease of AMH secretion caused by ovarian injury, and the curative effects are definite.

According to the Above Experimental Results, it can be Known as Follows:
(1) Seabuckthorn fruit pulp and Sea buckthorn seed oil can prevent and treat mouse ovarian atrophy caused by ovarian injury, and improve the morphology of ovarian tissue.
(2) Seabuckthorn fruit pulp and Sea buckthorn seed oil can prevent and treat the estrous cycle disorders of mice caused by ovarian injury, and maintain the normal physiological cycle of mice.
(3) Seabuckthorn fruit pulp and Sea buckthorn seed oil can prevent and treat mouse hypoestrogenism caused by ovarian injury.
(4) Seabuckthorn fruit pulp and Sea buckthorn seed oil can prevent and treat the damage of ovarian reserve caused by ovarian injury in mice.
(5) In view of the similarity of mouse ovarian injury induced by radiotherapy, chemotherapy and external environment changes, Sea buckthorn fruit pulp and Sea buckthorn seed oil would have preventive, protective and therapeutic effects on ovarian injury and ovarian dysfunction caused by various external factors.

It should be understood that those skilled in the art will readily conceive other embodiments of the application after considering the specification and practicing the application disclosed herein. This application is intended to encompass any variations, uses, or adaptive changes of this application. These variations, uses, or adaptive changes conform to the general principles of this application and include common knowledge or customary technical means in the technical field which are not disclosed in this application. The description and the embodiments will only be considered exemplary, and the real scope and spirit of the application are indicated by the following claims.

It should be understood that this application is not limited to what has been described above, and various modifications and changes can be made without departing from its scope. The scope of the application is only limited by the appended claims.

What is claimed is:

1. A method for treating ovarian injury induced by chemoradiotherapy in a subject in need thereof, comprising administering to the subject an effective amount of a composition comprising fruit pulp or seed oil of Sea buckthorn (*Hippophae rhamnoides Linn*), or a combination thereof.

2. The method according to claim 1, wherein the dosage forms of the composition include powder, decoction, soft capsule, dripping pill, emulsion, tablet, lotion, liniment, ointment or suppository.

3. The method according to claim 1, wherein the ovarian injury includes estrous cycle disorder, excessive activation and consumption of follicles, decreased follicular reserve, follicle formation disorder, follicular maturation disorder, decreased estrogen, early withdrawal of estrogen, and decreased AMH.

4. The method according to claim 1, wherein the composition is provided in the form of medicament, health product, or functional food.

* * * * *